(12) United States Patent
Kraft et al.

(10) Patent No.: US 6,710,362 B2
(45) Date of Patent: Mar. 23, 2004

(54) DEVICE FOR IRRADIATING A TUMOR TISSUE

(75) Inventors: Gerhard Kraft, Darmstadt (DE); Ulrich Weber, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 10/239,685

(22) PCT Filed: Jul. 2, 2001

(86) PCT No.: PCT/EP01/07553
§ 371 (c)(1),
(2), (4) Date: Jan. 8, 2003

(87) PCT Pub. No.: WO02/07817
PCT Pub. Date: Jan. 31, 2002

(65) Prior Publication Data
US 2003/0136924 A1 Jul. 24, 2003

(51) Int. Cl.[7] ................................. A61N 5/00
(52) U.S. Cl. ................................. 250/492.3
(58) Field of Search ............ 250/492.1, 492.3, 250/505.1

(56) References Cited

U.S. PATENT DOCUMENTS 5,039,867 A * 8/1991 Nishihara et al. ......... 250/492.3
6,144,875 A * 11/2000 Schweikard et al. ......... 600/427

FOREIGN PATENT DOCUMENTS

EP 0 986 070 A1 9/1998

* cited by examiner

Primary Examiner—John R. Lee
Assistant Examiner—Christopher M. Kalivoda
(74) Attorney, Agent, or Firm—Frommer Lawrence & Haug LLP; Ronald R. Santucci

(57) ABSTRACT

The invention relates to an apparatus and a method for irradiating tumor tissue (3) of a patient (10) by means of an ion beam (2). For that purpose, the apparatus has a deflecting device (1) for the ion beam (2) for slice-wise and area-wise scanning of the tumor tissue (3) and an ion beam energy control device for slice-wise and depth-wise scanning of the ion beam (2). An electromechanically driven ion-braking device (11, 12) is provided as a depth-wise scanning adaptation apparatus (5) for adapting the range of the ion beam (2) and has faster depth-wise adaptation than the energy control device of an accelerator. The movement of a patient is monitored by means of a movement detection device (7) for detecting a temporal and positional change in the location of the tumor tissue (3) in a treatment space (8). A control device controls the deflecting device (1) and the depth-wise adaptation apparatus (5) for adjusting the ion beam direction and ion beam range, respectively, when scanning the tumor tissue (3) in the course of temporal and positional change in the location of the tumor tissue (3) in the treatment space (8).

19 Claims, 6 Drawing Sheets

DEVICE FOR IRRADIATING A TUMOR TISSUE

BACKGROUND OF THE INVENTION

The invention relates to an apparatus and a method for irradiating tumour tissue of a patient by means of an ion beam, in accordance with the independent claims.

The most recently developed ion beam scanning apparatuses and methods, such as those on which, for example, the European Patent Application 98 117 256.2 is based, allow increased precision in the irradiation of deep-lying tumours.

Using those apparatuses and methods, the target volume, such as a tumour of a patient, is broken down into layers of identical range, which layers are then scanned area-wise in a grid pattern using an ion beam. The ion beam is brought into a treatment space in relation to a fixed coordinate system, the spatial angle of an ion beam axis in the treatment space being fixed or emission from different spatial angles being possible by means of a gantry.

In order for the tumour of a patient to be positioned in that fixed coordinate system of the irradiation space, the patient must first be brought into the correct desired position relative to that coordinate system so that the actually irradiated or scanned volume of the ion beam conforms to the planned target volume of the tumour in the patient. It is, moreover, necessary in the case of such known systems for the patient to be maintained in the desired position during irradiation. In order to maintain the desired position, complicated devices such as individually fabricated thermoplastic mask systems are used for fixing the patient in position, in order to adjust the patient with millimetre accuracy before irradiation and to stabilise the patient by means of the mask during irradiation. Using the known apparatuses and methods, it is accordingly possible only to irradiate spatially fixed target volumes such as, for example, tumours in the head and neck region and tumours close to the spinal column, wherein either the head alone is fixed in position by means of a suitable mask or a full body mask stabilises the spinal column.

Irradiation of moving target volumes, for example in the thoracic region, has not hitherto been possible using such methods. For example, breathing movement causes the target volume to be displaced by a few centimetres in the thoracic region and, as a result, the desired millimetre precision is made impossible. It is accordingly impossible to achieve fixing in position with millimetre accuracy when, at the same time, internal movements cause displacement of the target volume in the centimetre range. In addition, movement of the target volume whilst beam scanning is being carried out causes substantial dose non-uniformities.

Whereas it would be possible, in the case where the ions in the ion beam have constant energy, for the relatively fast, area-wise, grid-patterned scanning to follow, in terms of time, the lateral movements of the target volume in the centimetre range, the accelerator is not able to vary the energy sufficiently fast to follow the organ movements in terms of depth, for example as a result of breathing or heartbeat in the thoracic region of a tumour patient.

BRIEF SUMMARY OF THE INVENTION

The problem of the invention is to provide an apparatus and a method for irradiating tumour tissue of a patient by means of an ion beam, wherein the ion beam can be adapted to spatial and temporal change, especially spatial and temporal periodic changes in the target volume, both perpendicular to the beam direction and in terms of depth.

The problem is solved by the subject-matter of the independent claims. Features of preferred embodiments are defined in the dependent claims.

In accordance with the invention, the apparatus for irradiating tumour tissue of a patient by means of an ion beam has a device for deflecting the ion beam for slice-wise and area-wise scanning of the tumour tissue and has an accelerator having an ion beam energy control device for step-wise and depth-wise scanning of the ion beam. In addition, the apparatus has an ion-braking device, which is used as a depth-wise scanning adaptation apparatus for adapting the range of the ion beam and which has faster depth-wise adaptation than the energy control device of the accelerator. Furthermore, the apparatus has a movement detection device for detecting a temporal and positional change in the location of the tumour tissue in a treatment space and has a control device which controls the deflecting device and the depth-wise scanning adaptation apparatus for adjustment of the ion beam direction and ion beam range, respectively, when scanning the tumour tissue in the event of temporal and positional change in the location of the tumour tissue in the treatment space.

The apparatus according to the invention has the advantage that moving target volumes of a patient who is moving can be irradiated with the same precision as non-moving target volumes in a patient who is fixed in position. For that purpose, the movement detection device detects the movements of the patient during irradiation, and the irradiation points are correspondingly corrected with the aid of a control device. In principle, it is no longer necessary, in the case of this apparatus, for the patient to be initially adjusted with millimetre accuracy in the fixed spatial coordinates because, with the aid of the movement detection device, the actual initial location of a patient can also be adapted to the treatment program and/or the treatment program corrected accordingly.

In a preferred embodiment of the invention, the apparatus has two electromagnets, by means of which the deflecting apparatus makes possible area-wise scanning. The electromagnets deflect the ion beam orthogonally to the ion beam axis in an X direction and a Y direction, which are, in turn, perpendicular to one another, in order to provide area-wise scanning of the tumour tissue which, relative to depth-wise scanning by means of the ion beam energy control device, is fast. For that purpose, the electromagnets are controlled by fast-reacting power units and measurement devices. Those devices can accordingly also be used to carry out correction and adaptation when scanning tumour tissue in the case of temporal and positional change in the location of the tumour tissue in the treatment space orthogonally to the ion beam axis.

In a preferred embodiment of the invention, the apparatus has at least one accelerator, by means of which the energy of the ion beam is adjustable so that the tumour tissue can be irradiated slice-wise, staggered in terms of depth. That is associated with the advantage that the entire tumour tissue can be successively scanned slice-wise, the range of the ion beam being adjustable from slice to slice by modifying the energy of the ion beam. For that purpose, the accelerator consists essentially of a synchrotron or a synchrocyclotron, in which ions of equal mass and equal energy can be accelerated step-wise to higher energies. Because of the complexity of the control functions for the accelerator, the energy of the ion beam cannot be adapted to specified ranges within the irradiation space or within the tumour volume sufficiently quickly or with the requisite precision for it to be possible to follow the movements of the tumour tissue, or patient, automatically.

In a preferred embodiment of the invention, the depth-wise scanning adaptation apparatus therefore has two ion-braking plates of wedge-shaped cross-section, which cover the entire irradiation field of the ion beam and allow fast depth-wise scanning adaptation in the case of moving tumour tissue.

For that purpose, in a preferred embodiment of the invention, the ion-braking plates are arranged on electromagnetically actuatable carriages. With the aid of those electromagnetically actuatable carriages, the position of the wedge-shaped ion-braking plates can be changed within milliseconds and, accordingly, the length of the braking path of the ions provided in an overlap region of the wedge-shaped braking plates can be varied by the ion-braking plates. For that purpose, the ion-braking plates overlap in the entire irradiation field of the ion beam and can accordingly adapt the ions in terms of their range, irrespective of their position, to positional and temporal changes in a moving target volume.

In a preferred embodiment of the invention, the ion-braking plates are mounted on linear motors. Such linear motors have the advantage that continuous, fine regulation of ion braking is possible for adaptation of depth-wise scanning of the target volume. Changing the position of the wedge-shaped ion-braking plates with the aid of linear motors is, moreover, not only extremely precise positionally but is also adaptable with extreme speed of reaction to temporal change in the target volume in terms of depth.

In a further embodiment, a water-filled cylinder of variable thickness is used instead of the wedges. The covers of the cylinder are made from transparent plates, for example from two plexiglass or silica glass panes, the upper pane of which is moved by 2 or 4 high-performance linear motors. The side covering of the cylinder is in the form of a bellows made from steel or rubber. Variation of the thickness of the water layer is assisted by a hydraulic system which, when the cylinder is drawn apart, pumps water into the cylinder and, when it is pressed together, draws water out so that the drive is spared and the formation of vacuoles is prevented.

This embodiment has the advantage that a smaller minimum thickness is possible than in the case of the wedges. In the case of the wedges, the minimum thickness is calculated from the wedge slope×field size (typically 5 cm). In the case of the cylinder arrangement, the minimum thickness is given by the thickness of the two covers (typically 1 cm). That small minimum thickness reduces the beam scatter and accordingly improves the beam quality. The cylinder arrangement is, moreover, more compact than the wedge construction in the transverse direction.

In a further preferred embodiment of the invention, the movement detection device has at least two measurement sensors which, from two spatial angles in relation to an ion beam axis, detect the temporal and positional location of markings on a region of the body of a patient containing tumour tissue. Such markings can be applied using skin-compatible luminous colours in the form of dots, dashes or other geometric shapes or in the form of luminous elements so that they can be clearly detected and measured by the measurement sensors.

In a further preferred embodiment of the invention, the measurement sensors are precision video cameras, which co-operate with an image-evaluating unit. By that means it is advantageously possible for the movements of a region of the body in the vicinity of tumour tissue to be exactly measured and correlated to the temporal and positional changes in the location of the tumour tissue.

Alternatively to the movement detection system which uses markings on the surface of the body and a precision video camera, a further embodiment of the invention has an X-ray system, which detects the movements of the tumour tissue directly in the body. In the case of that movement detection system, two X-ray tubes are mounted with their beam directions orthogonal to the ion beam. The two X-ray tubes are, in turn, also oriented perpendicular to one another. In addition, two sensitive X-ray image intensifiers are in each case mounted opposite, on the other side of the patient. The X-ray tubes emit short X-ray flashes of low power, in order to keep the dosage low, at a frequency of, for example, 20 Hz. The associated X-ray images are recorded by the image intensifiers and digitised. As a result, an image sequence for two directions is obtained, from which, using a suitable method and appropriate software, the displacement of the target points $P_1$ is determined in virtually real time with a delay of approximately 50 ms.

That embodiment has the advantage that much more information on movements in the interior of the body is obtained from the X-ray recordings than from external markings on the surface of the body, allowing more precise determination of temporal and positional organ displacements.

In principle, irradiation of the tumour volume is made up from image points, which are set beside one another area-wise in a grid pattern in the form of a slice, the ion beam being deflected from scanning point to scanning point orthogonally to its beam axis in an X direction and a Y direction. Even though the energy of the ions in an ion beam can be kept constant by the accelerator in question, the number of ions per volume point is not constant over time. In order, nevertheless, to beam an ion beam dose of equal magnitude into every volume point of the tumour tissue, an ionisation chamber having a fast read-out for monitoring the intensity of the ion beam flow is, in a preferred embodiment of the invention, arranged as a transmission counter in the beam path of the ion beam. Such a transmission counter determines the dwell time of the ion beam at a volume point being irradiated in the tumour volume, and a control unit connected thereto diverts the ion beam to the next volume point as soon as a specified beam dose has been achieved. It is, consequently, advantageously possible to scan a volume slice of a tumour volume area-wise in a grid pattern.

The ionisation chamber is preferably arranged between the deflecting device and the depth-wise scanning adaptation apparatus, especially as the depth-wise scanning adaptation apparatus having its wedge-shaped braking plates or the water layer between transparent plates merely controls the ions in terms of their range without, however, influencing the ion dose.

A method of irradiating tumour tissue of a patient by means of an ion beam comprises the following method steps:
  placing the patient on an apparatus matched to the contour of the patient for the purpose of positioning the patient in an irradiation space,
  applying markings to a region of the body of the patient, close to the tumour tissue,
  determining the temporal and positional change in the markings by means of a movement detection device or capturing X-ray images of the tumour tissue from two mutually perpendicular directions of X-ray beams orthogonal to the ion beam, adjusting the ion beam, whilst scanning the tumour tissue using an ion beam deflecting device and an ion beam energy control device, by means of an additional depth-wise scanning adaptation apparatus, which adapts the range of the ion beam to the temporal and positional changes in the markings, determined by the movement detection device, in co-operation with the ion beam deflecting device.

Using that method, it advantageously becomes possible to achieve the same precision in the millimetre range when irradiating moving tumour volumes in a patient who is moving as in the case of the patient who is fixed in position, even when the tumour tissue moves up to several centimetres periodically, for example as a result of heartbeat or breathing air. In this method, ion beam irradiation continuously follows the temporal and positional change in the location of the tumour tissue and it is not necessary to delay the irradiation until a repeating positional location has been achieved. Slow movements of the patient that occur on a non-periodic basis are also allowable and ion irradiation thereof can, with the aid of the depth-wise adaptation apparatus and the deflecting device, be adapted temporally and positionally. Only in the case of sudden changes in location such as fits of coughing does the irradiation procedure have to be suspended.

Compared to methods that allow irradiation only when identical locations of the tumour tissue have been achieved, the method according to the invention has the advantage that the irradiation time for a patient can be significantly shortened because the irradiation procedure is not dependent on, for example, the periodicity of the heartbeat or of the breathing of a patient.

Further advantages and features of the present invention will be described below in further detail with respect to embodiments with reference to the accompanying drawings.

DETAILED DESCRIPTION OF THE INVENTION

Figure 1:
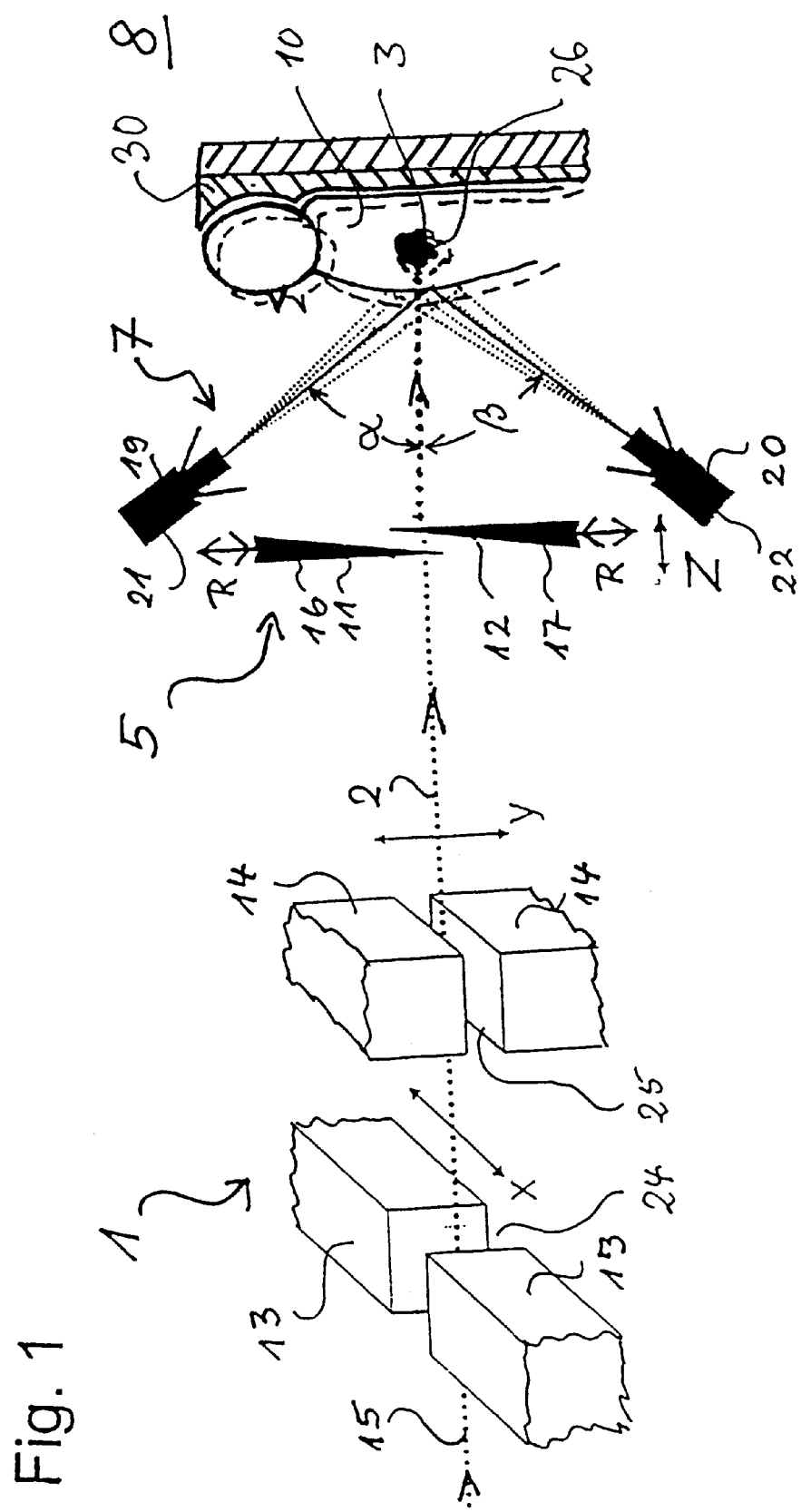
FIG. 1 is a representation, in diagrammatic form, of an embodiment of the invention in the course of irradiating tumour tissue in the thoracic region of a patient.

FIG. 1 is a representation, in diagrammatic form, of an embodiment of the invention in the course of irradiating tumour tissue 3 in the thoracic region 23 of a patient 10. For that purpose, the apparatus has an ion beam 2, which is deflected from its ion beam axis 15 by means of an ion beam deflecting device 1 orthogonally to the ion beam axis 15, more specifically in an X direction on passing through a gap 24 in an electromagnet 13 and in a Y direction on passing through a gap 25 in an electromagnet 14, the gaps being arranged perpendicular to one another.

Before impinging upon the tumour tissue 3 of a patient, the ion beam further passes through an ion-braking device 11, 12, electromagnetically driven in arrow direction R, which is used as a depth-wise scanning adaptation apparatus 5 for adapting the range of the ion beam 2 and which has faster depth-wise adaptation than an energy control device (not shown), by means of which the energy of the ion beam is controlled before entering the gaps 24, 25 in the electromagnets 13 and 14.

The ion beam energy control device (not shown) brings about staggered depth-wise scanning of the tumour tissue 3; as a result of increasing the energy in step-wise manner after each slice-wise and area-wise scan the ion beam penetrates deeper into the tumour tissue so that, in the end, the entire tumour tissue is destroyed as a result of slice-wise and depth-wise scanning of the ion beam.

On movement of the patient 10 depicted in this instance into a position shown by a broken line, the location of the tumour tissue 3 is also displaced so that in the case of static irradiation, which is unable to follow the movement of the patient, healthy tissue would be irradiated and destroyed.

In order to avoid that, the apparatus in FIG. 1 has a movement detection device 7 for detecting a temporal and positional change in the location of the tumour tissue 3 in a treatment space 8. That movement detection device 7, which in this embodiment of the invention consists of two precision video cameras 21 and 22, follows the movement of markings on a region of the body of the patient 10 and is communication with an image-evaluating device, which correlates the detected changed values of the markings with the temporal and positional change in the location of the tumour tissue 3.

A control device (not shown in FIG. 1) controls both the deflecting device 1 having the two electromagnets 13 and 14 and the depth-wise scanning adaptation apparatus having the ion-braking device 11, 12 for adjusting, on the one hand, the ion beam direction and, on the other hand, the ion beam range when scanning the tumour tissue in the case of temporal and positional change in the location of the tumour tissue 3 in the treatment space 8. Using the apparatus shown in FIG. 1, greater precision of beam application and, consequently, improved clinical success are achieved in the more than 100-year history of the development of beam therapy.

The continued increase in precision has resulted in the use of this scanning system comprising two electromagnets arranged perpendicular to one another, through the gaps of which magnets an ion beam is guided and deflected. When the apparatus according to FIG. 1 is used, the target volume, namely the tumour tissue 3, is scanned with a fine beam of ions at variable intensity. The diameter of that ion beam is in the millimetre range and the precision with which the target volume can be subjected to an ion dose is likewise in the range of a few millimetres.

In the event of displacement of the target volume 26 during irradiation, there arises a discrepancy between the actual beam focus and the actual target point and, consequently, incorrect irradiation inside the target volume 26, which is associated with local under-dosage or over-dosage. Scanning methods without the apparatus of the invention according to FIG. 1 cannot, therefore, be used currently in the case of moving target volumes 26.

Other irradiation apparatuses operate with a highly opened-out beam bundle and with a likewise very highly spread-out dose maximum in terms of depth. Such opened-out beam bundles can cover the entire target volume without area-wise and slice-wise scanning and, by virtue of the large irradiation field, they do not produce dosage non-uniformities inside the target volume as would be the case if slice-wise scanning apparatuses were to be used in the case of a moving target volume. In the case of apparatuses having an opened-out beam bundle, the movement of organs has an effect only at the edge and can therefore be compensated by enlarging the irradiation volume so that moving parts of the target no longer leave the irradiation volume. However, that means, conversely, that a large region of normal healthy tissue at the edge of the target volume also has to be irradiated so that, using an opened-out beam bundle whilst there is at the same time movement of the irradiated body, reduced precision and at the same time increased negative side-effects are the consequence for the patient.

Using an apparatus as shown in FIG. 1, but without a depth-wise scanning adaptation apparatus 5, organ movements can be taken into account only if the cross-section of the ion beam 2 is made substantially larger. Such a solution means, however, that precision in the lateral region is likewise reduced, and in the longitudinal dose profile no correction is made because, with beam opening-out, the movement in the beam direction cannot be corrected. Consequently, if opening-out of the beam is used for covering organ movements, the result is still non-uniform dosage distribution in the internal target volume in the beam direction.

A further possibility for using the apparatus according to FIG. 1 without a depth-wise scanning adaptation apparatus 5 and nevertheless taking organ movements into account can comprise detecting periodic movements of, for example, the thoracic region of a patient with the aid of the movement detection device 7 and carrying out irradiation only when the thorax assumes identical positions. Such an apparatus, wherein no depth-wise scanning adaptation apparatus is provided but wherein the periodic movement of the thorax of a patient is detected, would increase the irradiation and treatment time for a patient many times because, for each volume point in the slice-wise scanning of the tumour volume, it is necessary first to wait for the tumour to be in an identical position. Only opening-out of the beam can reduce the treatment time to realistic values in this instance, which is, in turn, as mentioned above, associated with a loss of precision.

Consequently, the apparatus according to the invention proves to be the approach by means of which the depth of penetration of the ion beam can be optimally adapted to the organ movements of a patient so that tumour tissue can be very precisely irradiated with millimetre accuracy in the event of temporal and positional change in location.

Figure 2:
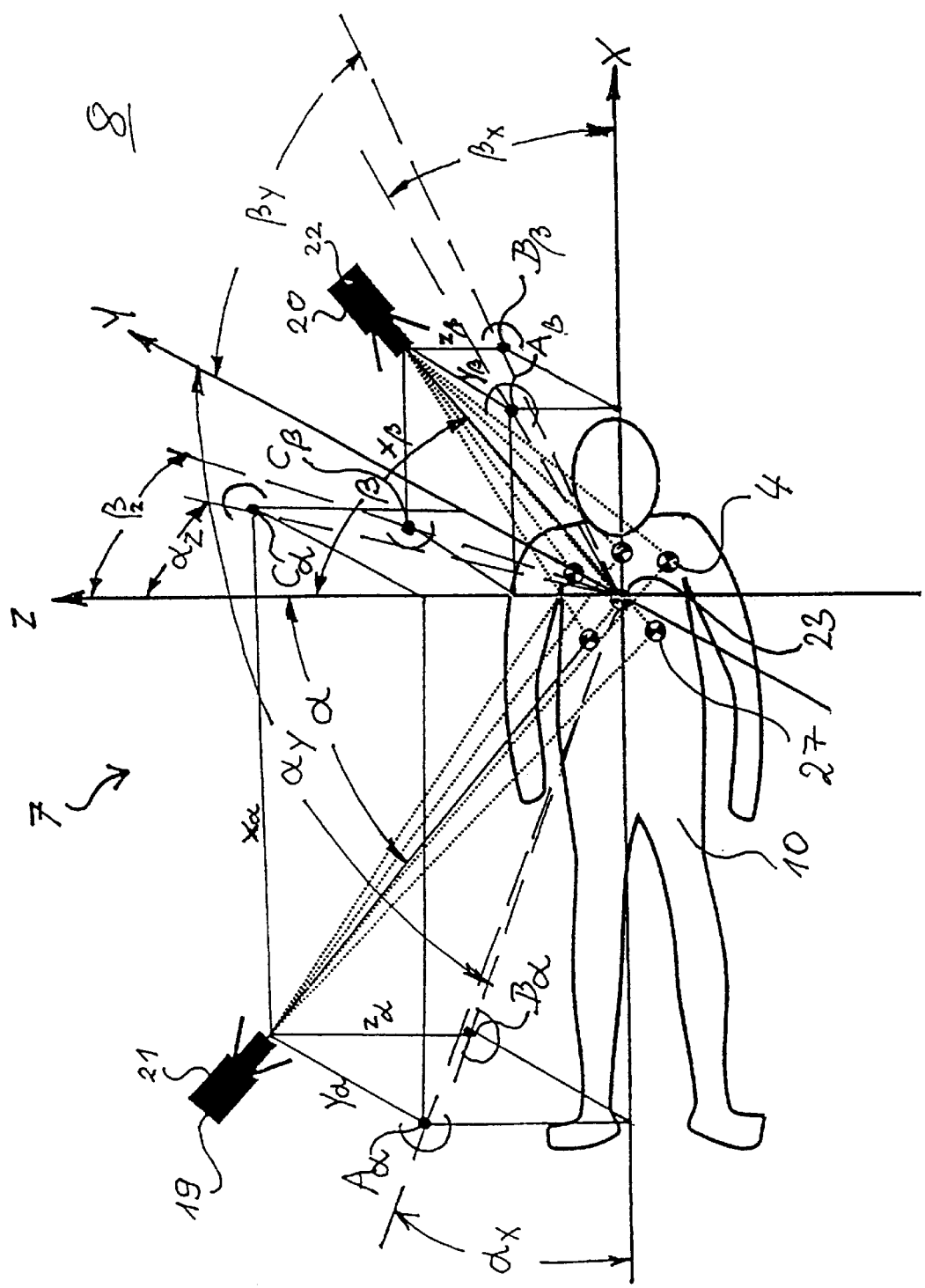
FIG. 2 is a representation, in diagrammatic form, of an embodiment of a movement detection device.

FIG. 2 is a representation, in diagrammatic form, of an embodiment of a movement detection device 7. This embodiment ascertains the movement of a region of the body of a patient 10 by means of two precision video cameras 21 and 22, which detect markings 4 on the thorax of a patient 10 from two different spatial angles, $\alpha$ and $\beta$, and send them to an image-evaluating unit (not shown). The markings 4 are so selected that, on the one hand, they are arranged in the vicinity of the tumour tissue to be irradiated and, on the other hand, accurately capture the thorax movements so that it is possible to deduce, from the temporal and positional changes in the markings 4, the temporal and positional displacements of location of the tumour tissue.

In the Cartesian coordinate system of the irradiation space 8 having the coordinate directions X, Y and Z, the spatial angles $\alpha$ and $\beta$ have spatial angle components $\alpha_x$, $\alpha_y$ and $\alpha_z$ for the spatial angle $\alpha$ and $\beta_x$, $\beta_y$, and $\beta_z$ for the spatial angle $\beta$. The spatial angles $\alpha$ and $\beta$ are, by means of those components, clearly correlated to the coordinate system X, Y and Z in the irradiation space 8.

The position of a first precision video camera 21 in that arrangement has the projection points $A_\alpha$, $B_\alpha$ and $C_\alpha$, the projection point $A_\alpha$ passing through the plane generated by the coordinates X and Z, the projection point $B_\alpha$ passing through the plane generated by the coordinates Y and X and the projection point $C_\alpha$ passing through the plane generated by the coordinates Z and Y. The position of the second camera 22 has the projection points $A_{62}$, $B_{62}$ and $C_{62}$, the projection point $A_{62}$ passing through the plane generated by the coordinates X and Z, the projection point $B_{62}$ passing through the plane generated by the coordinates Y and X and the projection point $C_{62}$ passing through the plane generated by the coordinates Z and Y. By way of those projection points, the position of the precision cameras 21 and 22 is likewise clearly defined in the irradiation space 8, the coordinates of the spatial angle $\alpha$ of the first precision video camera 21 being $x_\alpha$, $y_\alpha$ and $z_\alpha$ and the coordinates of the spatial angle $\beta$ in the case of the position of the second precision video camera 1 being $x_\beta$, $y_\beta$ and $z_\beta$.

The largest organ movements and, consequently, the largest temporal and positional changes in the marking 4 occur in the lung region of a patient during breathing. In the central thoracic region 23, displacements having an amplitude of up to 1 cm and, at the edge of the lungs, up to 3 cm are found. As a result of breathing, those displacements are periodic. The displacement of the internal structures is correlated to the movements of the body surface. Optical monitoring and detection of the body surface by means of the precision video cameras 21 and 22 therefore supplies respective actual location coordinates for the internal structures. For that purpose, markings 4 in the form of coloured dashes, coloured dots or luminous elements such as light-emitting diodes can be applied to the body surface. As a result, it is advantageously possible, without invasive intervention, to capture the internal geometry of the patient at any point in time, and also the temporal course of the displacements of the internal structures and the speed of the movements in question.

Figure 3:
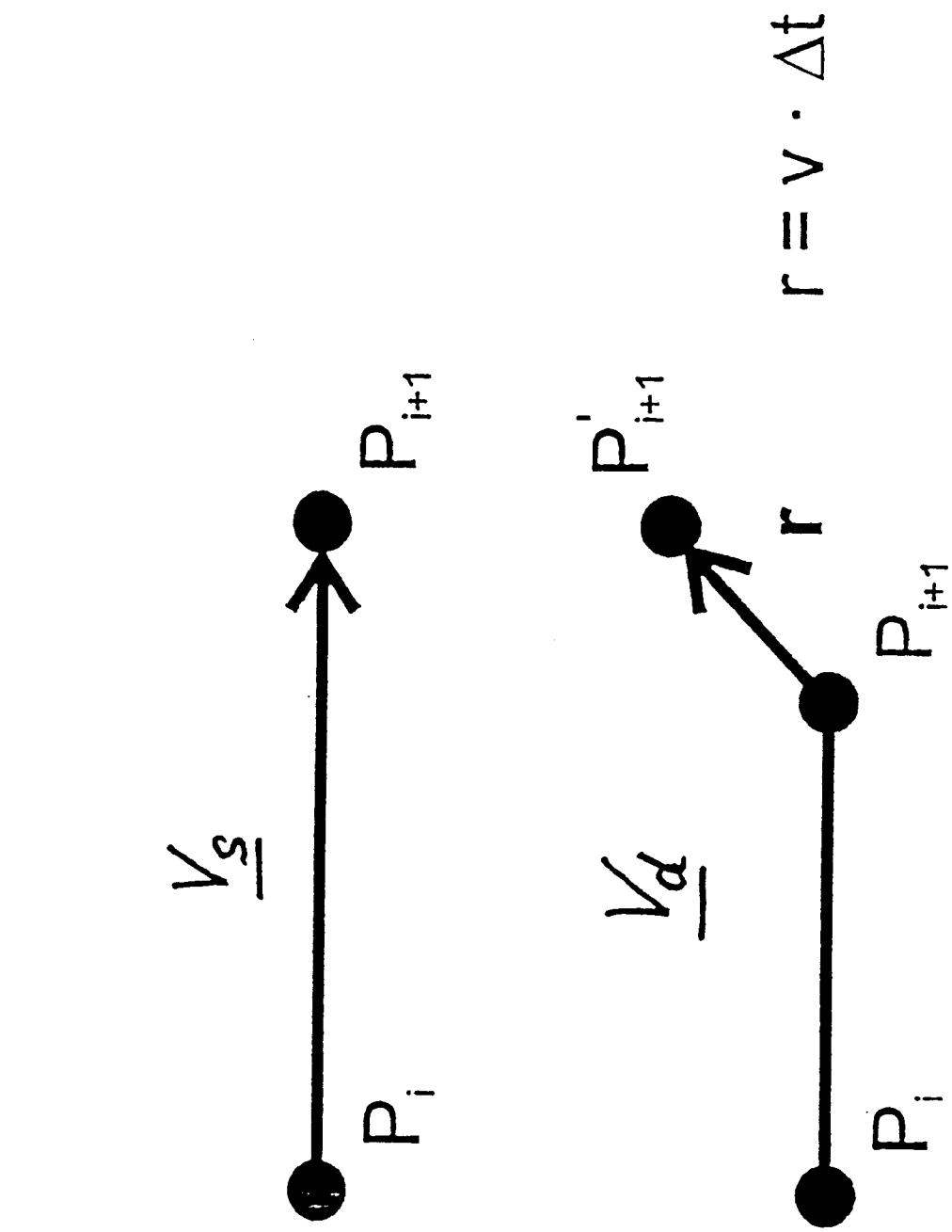
FIG. 3 shows a comparison between neighbouring volume scanning points in the case of a positionally and temporally fixed and, consequently, static, target volume and a positionally and temporally moving and, consequently, dynamic, target volume.

FIG. 3 shows a comparison between neighbouring volume scanning points $P_i$ and $P_{i+1}$ and $P'_{i+1}$ in the case of a positionally and temporally fixed, and consequently static, target volume $V_s$ and a positionally and temporally moving, and consequently dynamic, target volume $V_d$. The determination of the movement of the internal structures in correlation to the surface must be known before irradiation. That can be determined from model calculations or also from measurements.

Starting from a momentary recording at time-point t=0, it is possible, in the case of a short-time recording in a manner similar to the case of the grid scanning method for a non-moving object, for the target volume to be broken down into layers having a depth coordinate $z_i$ of equal particle range and each layer having a lateral network in the X and Y direction having reference image points, which cover volume scanning points $P_i$ ($x_i$, $y_i$, $z_i$). During irradiation, those image points are, by virtue of the movement, displaced to a position $P'_i(x_i+\Delta x_i(t) y_i+\Delta y_i(t) z_i+\Delta z_i(t))$. The discrepancies or displacements $\Delta x$, $\Delta y$ and $\Delta z$ result from the three-dimensional speed distribution of organ movement over time $\Delta t$, which is necessary for dose application at a volume point P of the tumour tissue 3. For example, a maximum displacement of the thoracic region 23 of 3 cm and a breath frequency of about 0.5 Hz, that is to say a duration of 2 s, results in a speed for the organ movements of about $v_{organ}=3$ cm/s.

The image points $P_i$, which then become volume scanning points, are, in the case of a lateral and longitudinal scanning procedure, spaced from 1 to 3 mm apart, that is to say after an irradiation dose at point $P_i$ the next neighbouring point at a distance of from 1 to 3 mm $P_{i+1}$ is accessed and a beam dose is again introduced at that volume scanning point. The time for application of the dose in a volume scanning point $P_i$ or $P_{i+1}$ is less than 10 ms. Consequently, the target point moves a maximum of 0.3 mm in that 10 ms, that is to say very much less than the spacing between two volume scanning points $P_i$ and $P_{i+1}$. Because the movement in the volume scanning point $P_i$ currently being irradiated is, during irradiation, less than the lack of sharpness of the irradiation, it is not necessary for the point $P_i$ to be displaced during its irradiation. After $P_i$ has been irradiated, the beam has to pass on to a point $P'_{i+1}$, which has been moved from the originally planned point $P_{i+1}$ in accordance with the coordinate movement of the organ. That organ movement is designated r in FIG. 3 and results from the speed, $r=v_{organ}\cdot\Delta t$. The actual position of the (i+1)th point is:

$$P'_{i+1}=(x_{i+1}+\Delta x_{i+1}(t), y_{i+1}+\Delta y_{i+1}(t), z_{i+1}+\Delta z_{i+1}(t))$$

The discrepancy or displacement of the moving points $P'_i$ from the originally static network of volume scanning points $P_i$ results from the displacement during the irradiation time. In the case of the usual cyclical and periodic movements such as breathing, heart rate etc. those points likewise follow a cyclic curve, which can be correlated to the movement of the body surface. Parameterising of the path over time is therefore possible. Using the apparatus according to the invention and the method according to the invention for irradiating tumour tissue of a patient by means of an ion beam, non-cyclic processes can be controlled only if the movement process does not occur suddenly but rather at a speed that is substantially slower than the scanning speed of the ion beam. In the event of sudden, hurried movements such as those occurring, for example, in the case of a coughing fit, the apparatus must be capable of being shut down at short notice in order to protect healthy tissue from receiving a dose in error.

Figure 4:
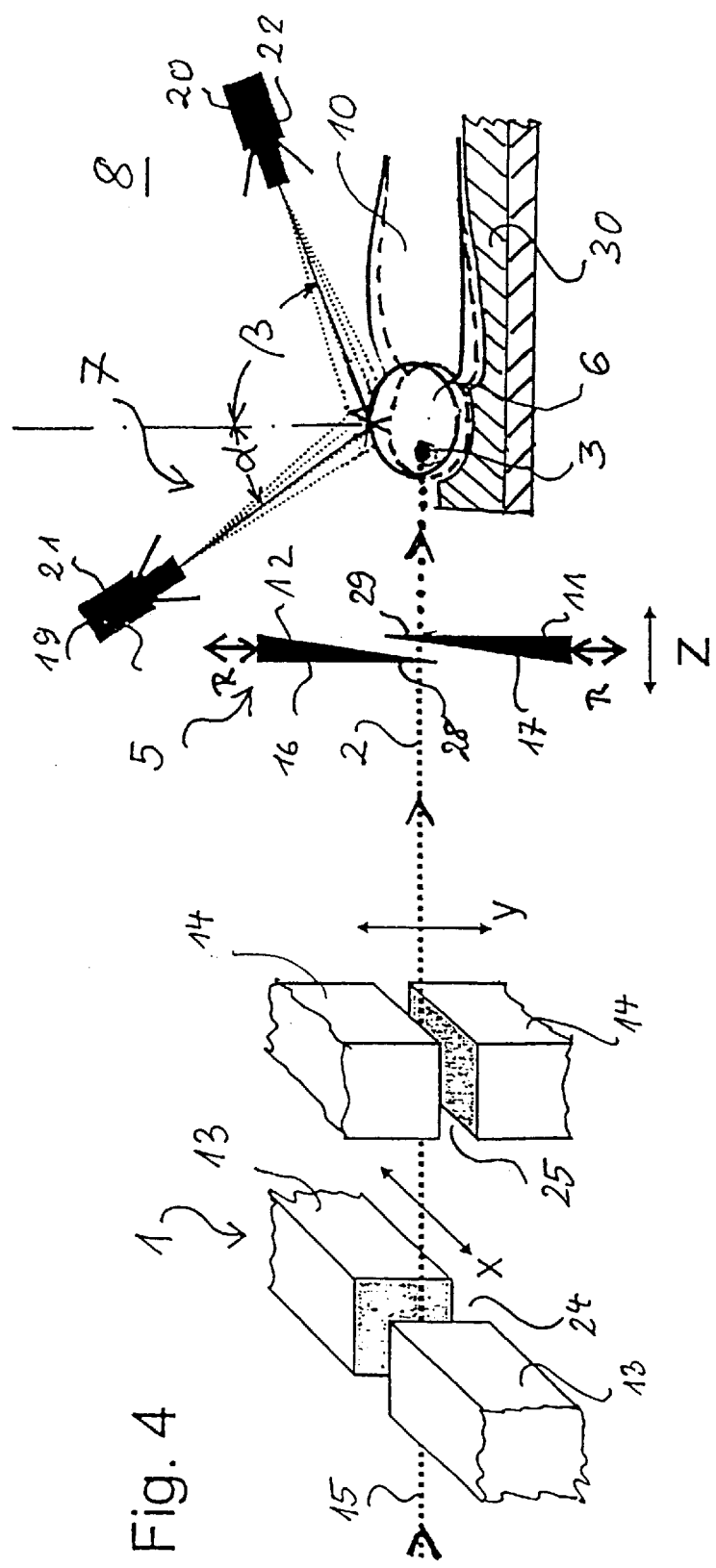
FIG. 4 is a representation, in diagrammatic form, of an embodiment of the invention in the course of irradiating tumour tissue in the head region of a patient.

FIG. 4 is a representation, in diagrammatic form, of an embodiment of the invention in the course of irradiating tumour tissue 3 in the head region 6 of a patient 10. The apparatus of FIG. 4 corresponds essentially to the apparatus according to FIG. 1 and likewise has two electromagnets 13 and 14 for deflecting the ion beam 2 from its axial direction 15, the range of the ion beam being controlled by ion-braking plates 16 and 17, which are wedge-shaped in profile. The overlapping regions 28 and 29 cover at least the entire irradiation region; by moving the wedge-shaped profiles of the braking plates 16 and 17 towards one another, the ion beam 2 braking path through the braking plates 16 and 17 is increased and, consequently, the range of the ion beam is reduced. By moving the wedge-shaped braking plates away from one another, the braking path is reduced and, consequently, the range of the ion beam is increased.

The direction of movement of the wedge-shaped braking plates 16 and 17 is indicated by the arrows R in FIG. 4. The displaceable braking plates having a wedge-shaped profile are, in this embodiment, driven by a high-performance linear motor so that beam-intensive controlled depth-wise adaptation can be accomplished. For the linear drive, the depth-wise scanning adaptation apparatus 5 has an electronic control system which co-operates with the movement detection device 7 and the deflecting device 1. In order to ensure fast reaction, the armatures of the linear motor, which carries the braking plates 16 and 17 on a carriage, are air-mounted and the motor currents of the linear motor are controlled by means of a servo motor control.

Figure 5:
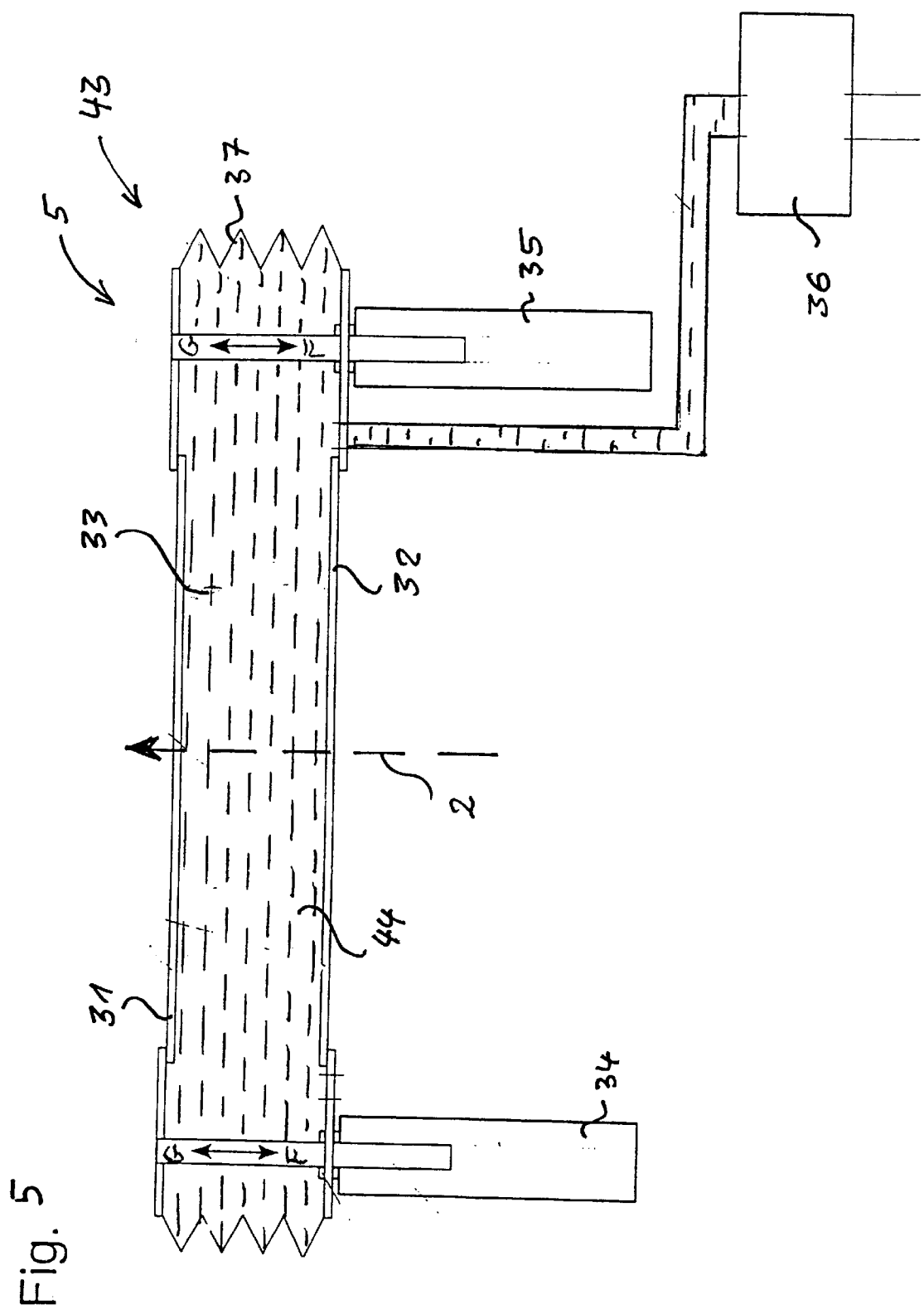
FIG. 5 is a representation, in diagrammatic form, of an ion-braking device by means of a variable water volume.

FIG. 5 is a representation, in diagrammatic form, of an ion-braking device 43 by means of a variable water volume. Components having identical functions to those in the preceding Figures are identified by identical reference symbols and are not separately described.

Reference symbol 44 denotes a layer of water, which is enclosed between two transparent plates 31 and 32. Of the transparent plates 31, 32, the plate 31 can be moved by means of linear motors 34 and 35. The number of linear motors can be increased as desired in order to increase the speed of displacement of the plate 31. The water layer 44 is safeguarded against outflow laterally by means of bellows 37. In order to take up the water volume or to add water, depending upon the direction of movement in arrow directions G and F, a compensating tank 36 is provided, which hydraulically assists the linear motors 34 and 35 by pumping in water when the water layer 44 is being increased and by drawing water off when the thickness of the water layer 44 is being reduced. Reference symbol 33 denotes the intermediate space filled with water. The ion beam 2 is passed through the water layer 44 for the purpose of braking and, in so doing, must also penetrate through the transparent plates 31 and 32, which can be made from glass or plexiglass. The smallest braking is achieved when the two plates 31 and 32 abut one another. They then also have an extremely small thickness, which minimises the scatter of the ion beam.

Figure 6:
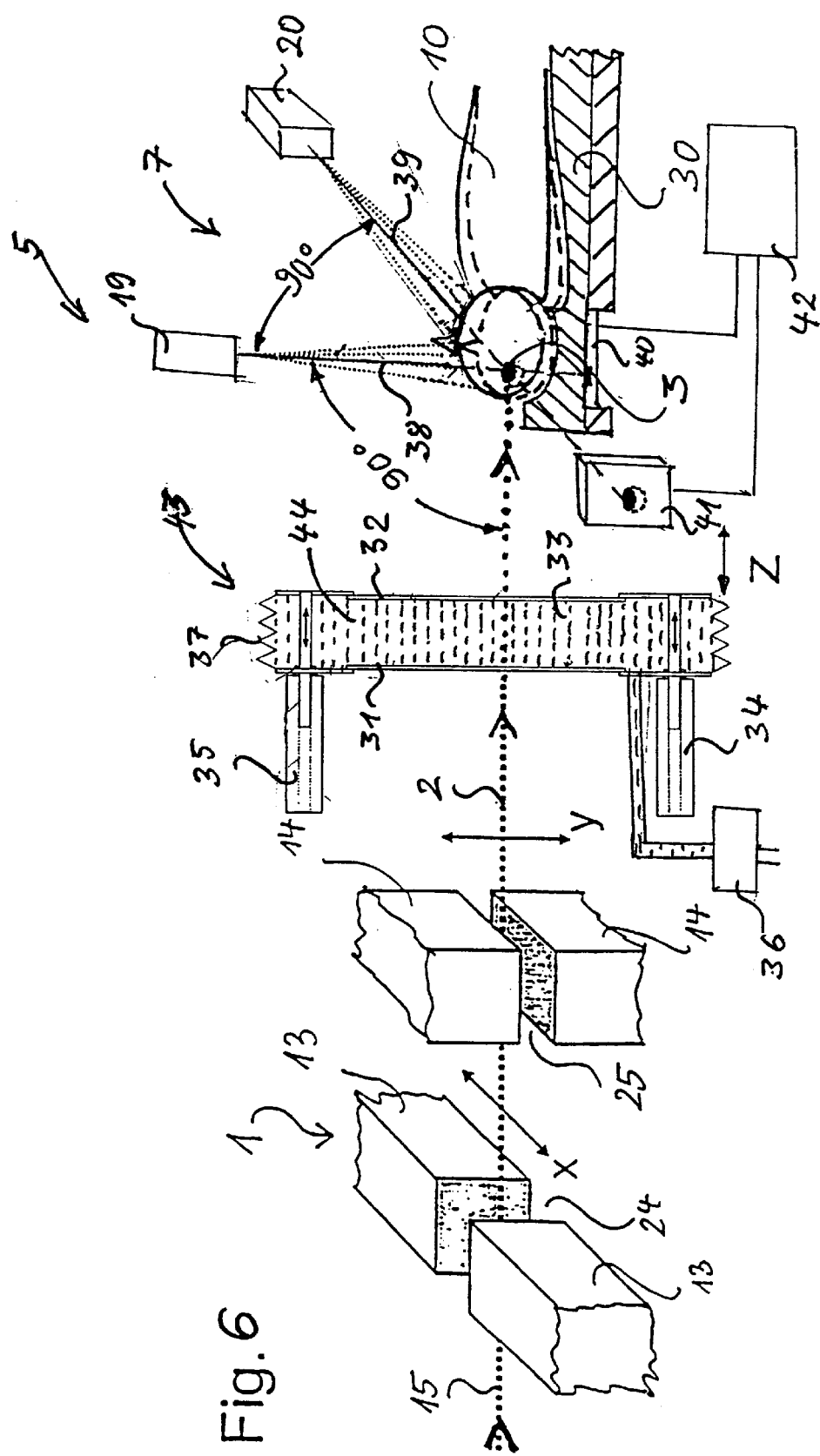
FIG. 6 is a representation, in diagrammatic form, of a further embodiment of the invention in the course of irradiating the tumour tissue in the head region of a patient.

FIG. 6 is a representation, in diagrammatic form, of a further embodiment of the invention in the course of irradiating tumour tissue 3 in the head region of a patient. Components having identical functions to those in the preceding Figures are identified by identical reference symbols and are not separately described.

This further embodiment differs from the embodiment according to FIG. 4 in that the wedge system is not used as the ion-braking device 43 but rather the braking device 43 shown in FIG. 5 is used. The further embodiment in FIG. 6 also differs from the embodiments in FIG. 1 and FIG. 4 in that a system comprising at least two X-ray tubes is used as the movement detection system. The measurement sensors 19 and 20 are X-ray tubes, which direct X-ray beams 38 and 39, at a right angle-to one another, at the tumour tissue 3 of the patient 10. Those X-ray beams are directed at the tumour tissue by X-ray flashes of low power at a frequency of, for example, 20 Hz and are received by corresponding image intensifier plates or sensor plates 40 and 41, which pass their signals on to the evaluating device 42. That movement detection system using X-ray beams is capable of directly following the movements of the tumour volume inside the body and, consequently, of controlling the braking device 43 very precisely.

FIRST EXAMPLE OF IMPLEMENTATION OF THE METHOD

In a first Example of implementation of the method, before irradiation, the surface of the patient is provided with significant markings such as, for example, coloured markings on the skin or light-emitting diodes etc. The patient is placed, for example, on a foam bed, as can be seen in FIG. 1 and FIG. 4 having reference numeral 30, which is adapted to his body. By that means, a positioning accuracy of about 1 cm can be achieved without constraint. In the irradiation position, as shown in the Figures FIG. 1 and FIG. 4, the patient 10 is monitored by a precision video system of at least two precision video cameras 21 and 22 from different spatial directions at spatial angles α and β, which record the position of the markings 4 (cf. FIG. 2) as a function of time and produce a time-dependent correction function for the image points or volume scanning points $P_i'(t)$.

In order to achieve fast displacement of the ion beam 2 in three dimensions, the lateral intensity-controlled grid scanner comprising two electromagnets 13 and 14 is combined with a depth-wise scanning adaptation apparatus 5, because in no ion accelerator is it possible for an ion beam energy control device to carry out fast energy variation during irradiation of a volume point P. The lateral scanning part, which as mentioned above comprises two electromagnets, whose deflection directions are arranged perpendicular to one another and to the beam axis 15, is controlled by fast power units so that rapid lateral scanning adaptation in the X and Y directions is ensured.

In addition to the scanning device 1 in the X and Y directions, there is arranged directly in front of the patient an electromechanically operated depth-wise scanning adaptation apparatus comprising essentially two wedges, which are mounted, working in opposite directions, on a linear motor and which cover the entire irradiation field. That depth-wise scanning adaptation apparatus serves only for correction of the depth-wise positional change in the image points caused by movement of the patient or of the patient's organs. That depth-wise scanning adaptation apparatus does not need to cover the entire depth of the target volume.

For coarse depth-wise variation, the energy variation of a synchrotron or other accelerator is used. In that process, the beam flow is monitored by means of an ionisation chamber installed in the beam path in front of the patient and is switched from a volume scanning point $P_i$ to the next scanning point $P_{i+1}$ when the necessary particle dose per volume scanning point P has been achieved. At the same time, in accordance with the precision video camera monitoring of the patient, the surface movement is measured, from which the movement of the internal structures in the target volume is calculated.

The magnetic values of the deflecting magnets and the depth-wise adaptation values of the wedge-shaped braking plates are corrected on the basis of the movement of the target points in three dimensions. The fact that the beam in this kind of method and apparatus is not interrupted during irradiation also means that there are no non-irradiated locations in the tumour tissue. The precision in the interior and also the sharp edge fall-off of static irradiation is consequently also achieved for moving organs with dynamic irradiation.

In addition, the apparatus and the method are invariable also with respect to compression of volume doses. In the case of volume compression, for example in the lungs, the image points come to lie closer together. As a result, the local particle fluence is increased. At the same time, the mass density is also increased as a result of the compression. Because the dose is defined as the energy deposition over density, it is unaffected by compression to a first approximation. That means that the particle movement of the individual beam positions does not need to be corrected during irradiation in the case of the apparatus according to the invention and the method according to the invention.

SECOND EXAMPLE OF IMPLEMENTATION OF THE METHOD

In a second Example of implementation of the method, instead of the marking on the body of the patient, the temporal and positional changes in the tumour tissue are ascertained directly by means of X-ray beams. For that purpose, after orientation of the patient, two X-ray beams are directed at the tumour tissue, which are arranged perpendicular to the ion beam 2 and which supply short X-ray flashes at low power in order to keep low the dose to which the patient is subjected. Those flashes can be directed at the tumour tissue at a frequency of 20 Hz. The X-ray beam directions are offset from another at 90° and together are arranged orthogonally with respect to the ion beam 2. By means of the X-ray beam flashes, image intensifier plates are illuminated, which pass their signals to an evaluating unit 42, which controls the braking device 43. The braking device 43 in this second Example of implementation of the invention is a water layer 33, the thickness of which is varied and which is arranged between two transparent plates 31 and 32. Fast variation of the water layer thickness is effected by modifying the intermediate space 33 between the two transparent plates 31 and 32. That displacement is carried out by linear motors 34 and 35, a compensating vessel 36 at the same time providing for pressure compensation and volume compensation of the water. All other irradiation steps for treating the tumour volume correspond to the method steps already described in the first Example of implementation.

LIST OF REFERNCE SYMBOLS 1 ion beam deflecting device
2 ion beam
3 tumour tissue
4 marking
5 depth-wise scanning adaptation apparatus
6 head region
7 movement detection device
8 treatment room
9 ion beam energy control device
10 patient
11, 12 ion-braking device
13 electromagnet for X deflection
14 electromagnet for Y deflection
15 ion beam axis
16, 17 ion-braking plates
19, 20 two measurement sensors
21, 22 two precision video cameras
23 thoracic region
24 gap in the electromagnet 13
25 gap in the electromagnet 14
26 target volume
27 edge of the lungs
28, 29 overlapping regions
30 foam bed
31, 32 transparent plates
33 intermediate space
34, 35 linear motors
36 compensation tank
37 bellows
38, 39 X-ray beams
40, 41 sensor plates
42 evaluating unit
43 ion-braking device
44 water layer
$V_s$ static target volume
$V_d$ dynamic target volume
P, $P_i$ volume scanning point
$P_{i+1}$ volume scanning point adjacent to $P_i$
α, β spatial angles
$α_x$, $α_y$, $α_z$ components of spatial angle α
$β_x$, $β_y$, $β_z$ components of spatial angle β

$x_\alpha$, $y_\alpha$, $z_\alpha$ coordinates of the spatial angle α at the first camera position $y_\beta$, $y_\beta$, $z_\beta$ coordinates of the spatial angle β at the second camera position $A_\alpha$, $B_\alpha$, $C_\alpha$ projection points onto the planes XZ ($A_\alpha$); YX($B_\alpha$); ZY($C_\alpha$) of the first camera position $A_\beta$, $B_\beta$, $C_\beta$ projection points onto the planes XZ ($A_\beta$); YX($B_\beta$); ZY($C_\beta$) of the second camera position

What is claimed is:

1. Apparatus for irradiating tumour tissue (3) of a patient (10) by means of an ion beam (2) having a deflecting device (1) for the ion beam (2) for slice-wise and area-wise scanning of the tumour tissue (3) and an accelerator having an ion beam energy control device for step-wise and depth-wise scanning of the tumour tissue (3), wherein the apparatus further has:

an electromechanically driven ion-braking device (11, 12), which is used as a depth-wise scanning adaptation apparatus (5) for adapting the range of the ion beam (2) and which has faster depth-wise adaptation than the energy control device of the accelerator, a movement detection device (7) for detecting a temporal and positional change in the location of the tumour tissue (3) in a treatment space (8), and a control device which controls the deflecting device (1) and the depth-wise scanning adaptation apparatus (5) for adjusting the ion beam direction and the ion beam range, respectively, when scanning the tumour tissue (3) in the course of temporal and positional change in the location of the tumour tissue (3) in the treatment space (8).

2. Apparatus according to claim 1, wherein the deflecting device (1) has two electromagnets (13, 14), which, for slice-wise and area-wise scanning of the tumour tissue (3), deflect an ion beam orthogonally to the ion beam axis (15) in an X direction and a Y direction, which are in turn located perpendicular to one another.

3. Apparatus according to claim 2, wherein the electromagnets are controlled by fast-reacting power units.

4. Apparatus according to claim 1, wherein the apparatus has accelerators by means of which the energy of the ion beam (2) is arranged to be so adjusted that the tumour tissue (3) can be irradiated slice-wise, staggered in terms of depth.

5. Apparatus according to claim 1, wherein the depth-wise scanning adaptation apparatus (5) has, for fast depth-wise scanning adaptation in the case of moving tumour tissue (3), an electromechanically operated ion-braking device which has two ion-braking plates (16, 17), which in cross-section are wedge-shaped and which cover the entire irradiation field of the ion beam (2).

6. Apparatus according to claim 5, wherein the ion-braking plates (16, 17) are mounted on linear motors.

7. Apparatus according to claim 5, wherein the ion-braking plates (16, 17) are arranged on electromagnetically actuatable carriages.

8. Apparatus according to claim 5, wherein the ion-braking plates are arranged to be displaced in opposite directions, their wedge-shaped cross-sections overlapping in the region of the ion beam (2).

9. Apparatus according to claim 1, wherein the depth-wise scanning adaptation apparatus (5) has, for fast depth-wise scanning adaptation in the case of moving tumour tissue (3) a hydraulically assisted ion-braking device wherein the thickness of a water layer (33) between two transparent plates (31, 32), through which the ion beam (2) is directed, is adapted to the movements of the tumour tissue.

10. Apparatus according to claim 9, wherein the two transparent plates (31, 32) are arranged to be moved towards one another and have water in their intermediate space (33).

11. Apparatus according to claim 9, wherein the spacing between the transparent plates (31, 32) and, consequently, the thickness of the water layer (33) are arranged to be adjusted by means of linear motors (34, 35).

12. Apparatus according to claim 9, wherein the depth-wise scanning adaptation apparatus (5) has a hydraulically operated compensation tank (36) for the water volume between the transparent plates (31, 32).

13. Apparatus according to claim 9, wherein a bellows (37) is arranged between the transparent plates (31, 32).

14. Apparatus according to claim 1, wherein the movement detection device (7) has at least two measurement sensors (19, 20), which detect, from two spatial angles (a, 13) in relation to an ion beam axis (15), the temporal and positional location of markings on a region of the body of a patient (10) that contains tumour tissue (3).

15. Apparatus according to claim 14, wherein the measurement sensors (19, 20) are precision video cameras (21, 22), which cooperate with an image-evaluating unit.

16. Apparatus according to claim 1, wherein the movement detection device (7) has at least two measurement sensors (19, 20), which are arranged orthogonally to the ion beam and perpendicular to one another, the temporal and positional change in the location of the tumour tissue being monitored by short pulses of X-ray beams (38, 39), and the movement detection device (7) having, for detection of the images of the tumour tissue, correspondingly arranged sensor plates (40, 41) and an evaluating unit (42).

17. Apparatus according to claim 1, wherein an ionisation chamber having a fast read-out for monitoring the intensity of the ion beam flow is arranged as a transmission counter in the beam path of the ion beam (2).

18. Apparatus according to claim 17, wherein the ionisation chamber is arranged between the deflecting device (1) and the depth-wise scanning adaptation apparatus (5).

19. Method of irradiating tumour tissue of a patient by means of an ion beam (2), which method comprises the following method steps:

placing the patient (10) on an apparatus matched to the contour of the patient for positioning the patient (10) in an irradiation space (8), applying markings to a region of the body of the patient (10), close to the tumour tissue (3), determining the temporal and positional change in the markings by means of a movement detection device (7) or capturing X-ray images of the tumour tissue from two mutually perpendicular directions of X-ray beams orthogonal to the ion beam, adjusting the ion beam (2), whilst scanning the tumour tissue using an ion beam deflecting device (1) and an ion beam energy control device by means of an additional depth-wise scanning adaptation apparatus (5), which adapts the range of the ion beam to the temporal and positional changes in the markings or tumour tissue, determined by the movement detection device (7), in co-operation with the ion beam deflecting device (1).

* * * * *